(12) United States Patent
Schmieding

(10) Patent No.: US 9,855,146 B2
(45) Date of Patent: Jan. 2, 2018

(54) ARTHROSCOPIC RESURFACING TECHNIQUES

(71) Applicant: ARTHREX, INC., Naples, FL (US)

(72) Inventor: Reinhold Schmieding, Naples, FL (US)

(73) Assignee: ARTHREX, INC., Naples, FL (US)

( * ) Notice: Subject to any disclaimer, the term of this patent is extended or adjusted under 35 U.S.C. 154(b) by 38 days.

(21) Appl. No.: 14/833,431

(22) Filed: Aug. 24, 2015

(65) Prior Publication Data

US 2017/0056180 A1    Mar. 2, 2017

(51) Int. Cl.
| | |
|---|---|
| *A61F 2/30* | (2006.01) |
| *A61F 2/38* | (2006.01) |
| *A61B 17/02* | (2006.01) |
| *A61F 2/42* | (2006.01) |
| *A61F 2/46* | (2006.01) |
| A61B 17/04 | (2006.01) |
| B33Y 10/00 | (2015.01) |
| B33Y 50/00 | (2015.01) |
| B33Y 70/00 | (2015.01) |
| B33Y 80/00 | (2015.01) |

(52) U.S. Cl.
CPC ........ *A61F 2/30756* (2013.01); *A61B 17/025* (2013.01); *A61F 2/30942* (2013.01); *A61F 2/3877* (2013.01); *A61F 2/4202* (2013.01); *A61F 2/4644* (2013.01); *A61B 17/0401* (2013.01); *A61B 2017/0268* (2013.01); *A61F 2002/30757* (2013.01); *A61F 2002/30948* (2013.01); *A61F 2002/30953* (2013.01); *A61F 2002/4207* (2013.01); *B33Y 10/00* (2014.12); *B33Y 50/00* (2014.12); *B33Y 70/00* (2014.12); *B33Y 80/00* (2014.12)

(58) Field of Classification Search
CPC .. A61F 2/07; A61F 2/08; A61F 2/4601; A61F 2/28; A61F 2/46; A61F 2/30756; A61F 2/3877

See application file for complete search history.

(56) References Cited

U.S. PATENT DOCUMENTS

| | | | |
|---|---|---|---|
| 7,879,105 B2 | 2/2011 | Schmieding et al. | |
| 8,077,950 B2 | 12/2011 | Tsougarakis et al. | |
| 8,172,907 B2 * | 5/2012 | Martinetti | A61F 2/28 |
| | | | 264/219 |
| 8,500,740 B2 | 8/2013 | Bojarski et al. | |

(Continued)

OTHER PUBLICATIONS

Senthil T. Nathan, et al., "Osteoarticular Allograft Reconstruction for Hill-Sachs Lesion in an Adolescent," Orthopedis, May 2012—vol. 35—Issue 5: e774-3747. DOI: 10.3928/01477447-20120426-33.

(Continued)

*Primary Examiner* — Jason-Dennis Stewart
(74) *Attorney, Agent, or Firm* — Carlson, Gaskey & Olds

(57) ABSTRACT

This disclosure relates to arthroscopic resurfacing techniques for treating diseased bone. The techniques include passing a graft into a joint and fixating the graft against an articulating surface of a bone of the joint. A method for resurfacing a bone according to an exemplary aspect of the present disclosure includes, among other things, sizing a graft based on a replicate of a bone, arthroscopically positioning the graft against an articulating surface of the bone, and securing the graft to the bone using at least one suture anchor.

16 Claims, 17 Drawing Sheets

(56) References Cited

U.S. PATENT DOCUMENTS

| | | |
|---|---|---|
| 8,690,960 B2 | 4/2014 | Hotter et al. |
| 8,709,089 B2 | 4/2014 | Lang et al. |
| 8,808,301 B1 | 8/2014 | Nofsinger |
| 8,882,847 B2 | 11/2014 | Burdulis, Jr. et al. |
| 8,894,713 B2 | 11/2014 | Shohat et al. |
| 8,951,259 B2 | 2/2015 | Fitz et al. |
| 2005/0038520 A1 | 2/2005 | Binette et al. |
| 2007/0270857 A1* | 11/2007 | Lombardo .......... A61B 17/0401 606/232 |
| 2008/0125863 A1 | 5/2008 | McKay |
| 2008/0188936 A1 | 8/2008 | Ball et al. |
| 2008/0281422 A1* | 11/2008 | Schmieding ........... A61B 17/04 623/16.11 |
| 2009/0060974 A1 | 3/2009 | Schmieding et al. |
| 2009/0062870 A1 | 3/2009 | Milano et al. |
| 2009/0204228 A1* | 8/2009 | Hiles ..................... A61K 35/37 623/23.72 |
| 2011/0238179 A1* | 9/2011 | Laurencin .......... A61B 17/1146 623/13.19 |
| 2013/0123930 A1 | 5/2013 | Burt |
| 2014/0094924 A1 | 4/2014 | Hacking et al. |
| 2015/0057750 A1* | 2/2015 | Timmerman ...... A61B 17/0401 623/13.14 |

OTHER PUBLICATIONS

Carticel Surgical Procedure, 17 pages, Last Update: Apr. 3, 2003; The Center for Orthopaedics and Sports Medicine, 1211 Johnson Ferry Rd., Marietta, GA 30068; http://www.arthroscopy.corn/sp08029.htm.

\* cited by examiner

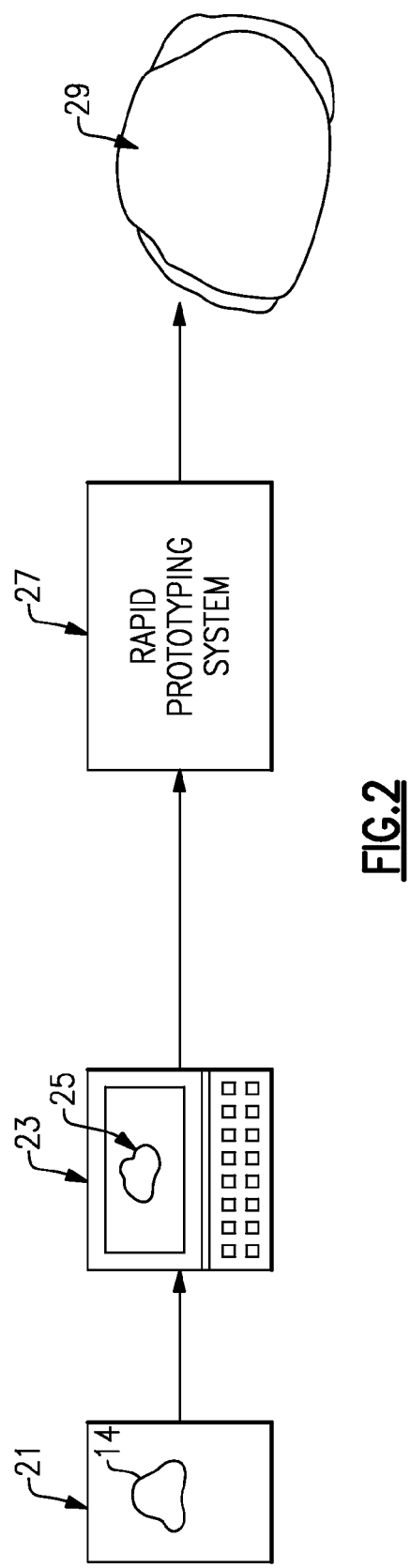

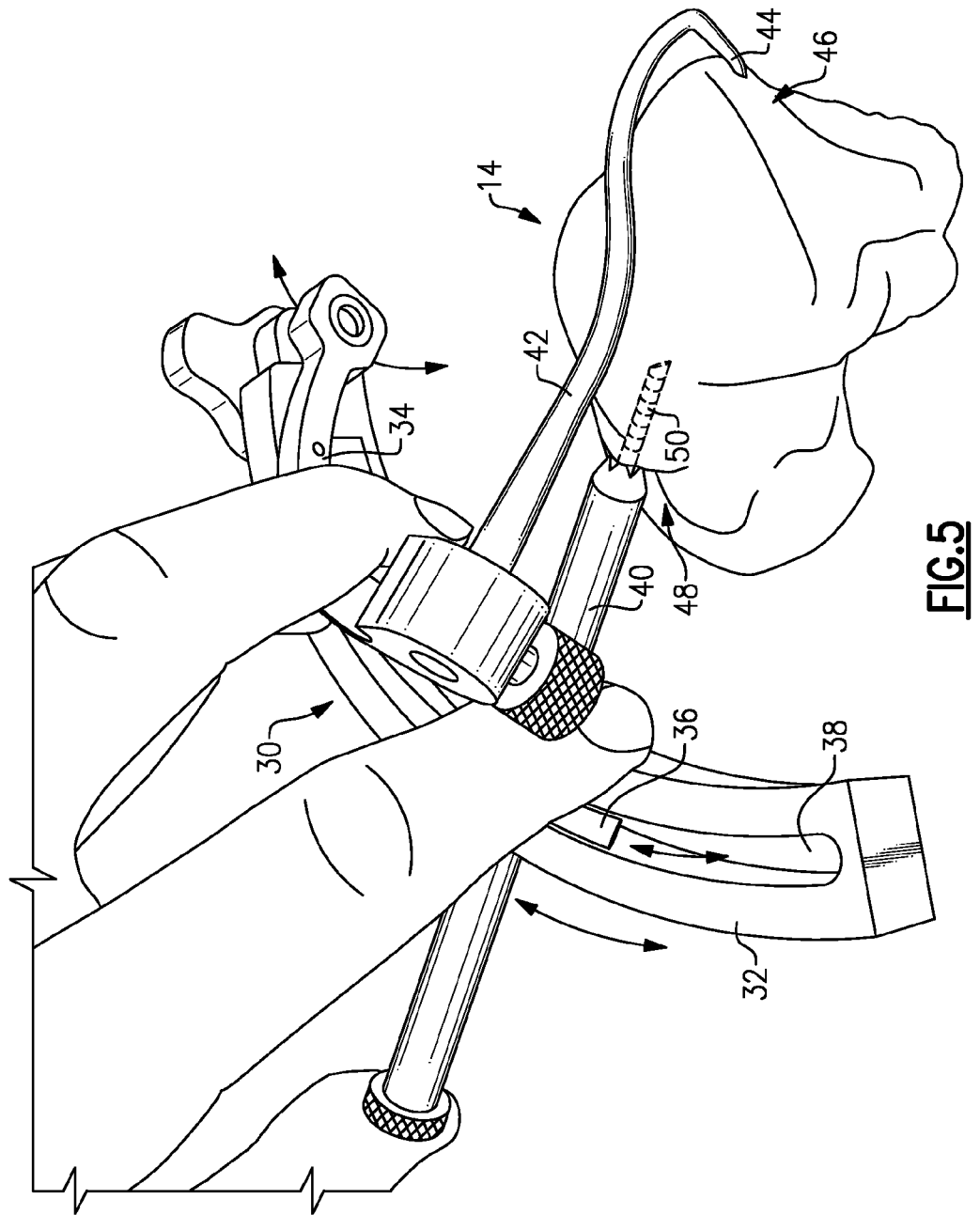

ARTHROSCOPIC RESURFACING TECHNIQUES

BACKGROUND

This disclosure relates to surgical methods for resurfacing bone to treat arthritic portions of bone.

Repetitive trauma to a joint, such as an ankle, knee, hip or shoulder joint, may damage bone, particularly at the articulating surfaces of the joint. If not treated, the damaged bone could lead to relatively significant arthritic pain and loss of motion. Over time, arthritis can cause the loss of articular cartilage. For some individuals, joint replacement surgery may be an undesirable option for alleviating severe arthritis pain and any associated loss of articular cartilage.

SUMMARY

This disclosure relates to arthroscopic resurfacing techniques for treating diseased bone. The techniques include passing a graft into a joint and fixating the graft against an articulating surface of a bone of the joint.

A method for resurfacing a bone according to an exemplary aspect of the present disclosure includes, among other things, sizing a graft based on a replicate of a bone, arthroscopically positioning the graft against an articulating surface of the bone, and securing the graft to the bone using at least one suture anchor.

In a further non-limiting embodiment of the foregoing method, the replicate of the bone is a rapidly prototyped model of the bone.

In a further non-limiting embodiment of either of the foregoing methods, the method includes obtaining a radiographical image of the bone, communicating the radiographical image to a computer system to generate a 3D model of the bone, and communicating the 3D model to a rapid prototyping system to create the replicate of the bone.

In a further non-limiting embodiment of any of the foregoing methods, the method includes practicing a surgical procedure on the replicate of the bone prior to performing the steps of arthroscopically positioning the graft and securing the graft to the bone.

In a further non-limiting embodiment of any of the foregoing methods, the graft is an acellular dermal extracellular matrix.

In a further non-limiting embodiment of any of the foregoing methods, the method includes creating a bleeding bone bed on the articulating surface prior to the step of arthroscopically positioning the graft.

In a further non-limiting embodiment of any of the foregoing methods, the method includes applying a bone marrow concentrate between the graft and the articulating surface after the step of securing the graft to the bone.

In a further non-limiting embodiment of any of the foregoing methods, the at least one suture anchor is a knotless suture anchor.

In a further non-limiting embodiment of any of the foregoing methods, the step of arthroscopically positioning the graft includes attaching a plurality of flexible strands to the graft and passing the graft into a joint space surrounding the bone using the plurality of flexible strands.

In a further non-limiting embodiment of any of the foregoing methods, the step of passing the graft into the joint space includes shuttling the plurality of flexible strands through tunnels formed in the bone using a shuttling device.

In a further non-limiting embodiment of any of the foregoing methods, the bone is a patella bone and the method includes passing a plurality of flexible strands through the graft, shuttling the plurality of flexible strands one by one into a joint space surrounding the patella bone, extracting free ends of each of the plurality of flexible strands through skin, pulling the graft into place against the articulating surface using the plurality of flexible strands and anchoring the graft to the patella bone using the at least one suture anchor.

In a further non-limiting embodiment of any of the foregoing methods, the bone is a talus bone and the method includes preparing crossing tunnels through the talus bone, passing sutures through the crossing tunnels, pulling the graft into place against the articulating surface of the talus bone using the sutures and anchoring the graft to the talus bone using the at least one suture anchor.

A method for resurfacing a bone according to another exemplary aspect of the present disclosure includes, among other things, distracting a bone from a joint, arthroscopically passing a graft into the joint, positioning the graft against an articulating surface of the bone, and fixating the graft to the bone using at least one suture anchor.

In a further non-limiting embodiment of the foregoing method, the step of distracting the bone from the joint includes inserting a second suture anchor into the bone, connecting a flexible strand that is attached to the suture anchor to a limb positioner, and moving the limb positioner to distract the bone from the joint.

In a further non-limiting embodiment of either of the foregoing methods, the step of connecting the flexible strand includes looping the flexible strand over an arm of the limb positioner.

In a further non-limiting embodiment of any of the foregoing methods, the step of moving the limb positioner includes pivoting the arm of the limb positioner between a first position and a second position.

In a further non-limiting embodiment of any of the foregoing methods, the articulating surface is a posterior articulating surface of the bone.

A surgical system according to another exemplary aspect of the present disclose includes, among other things, a limb positioner, a suture anchor and at least one flexible strand connected between an arm of the limb positioner and the suture anchor, the arm movable between a first position and a second position to distract a first bone away from a second bone.

In a further non-limiting embodiment of the foregoing surgical system, the limb positioner includes a body, the arm, an adjustment device and a stand.

In a further non-limiting embodiment of either of the foregoing surgical systems, the adjustment device is movable to pivot the arm.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 2 schematically illustrates a rapid prototyping technique for creating a bone replicate of the bone that is to be resurfaced.

FIG. 5 illustrates the positioning of a drill guide on a bone during a bone resurfacing procedure.

DETAILED DESCRIPTION

This disclosure describes surgical methods for resurfacing portions of arthritic or diseased bone. The resurfacing techniques include passing a graft into a joint and fixating the graft against an articulating surface of a bone of the joint. The resurfacing techniques may be performed to decrease pain and increase functionality of any joint of a musculoskeletal system.

In some non-limiting embodiments, the surgical methods include sizing a graft, arthroscopically positioning the graft against an articulating surface of the bone, and then securing the graft to the bone. In other non-limiting embodiments, the graft is secured to the bone using one or more suture anchors. In still other non-limiting embodiments, the graft is passed into a joint space and positioned relative to the bone using sutures. These and other features are described in detail in the following paragraphs of this detailed description.

Figure 1:
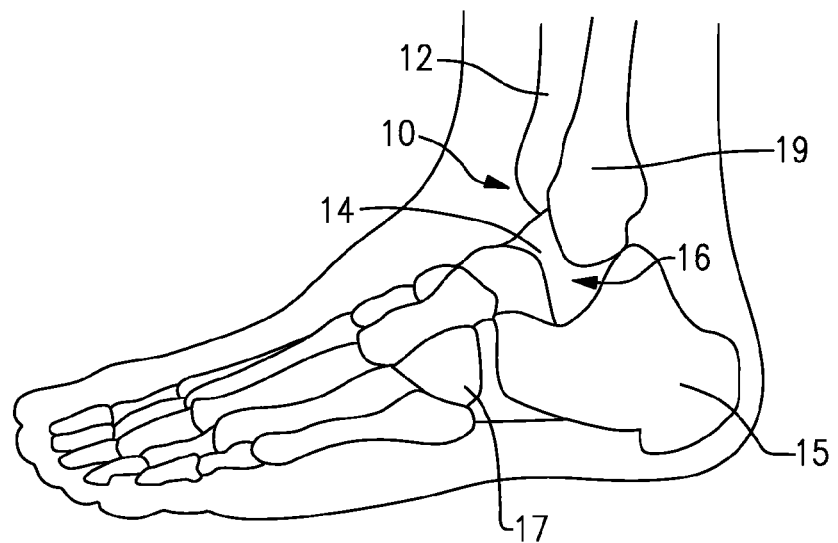
FIG. 1 illustrates a joint of a human musculoskeletal system.
Figure 3:
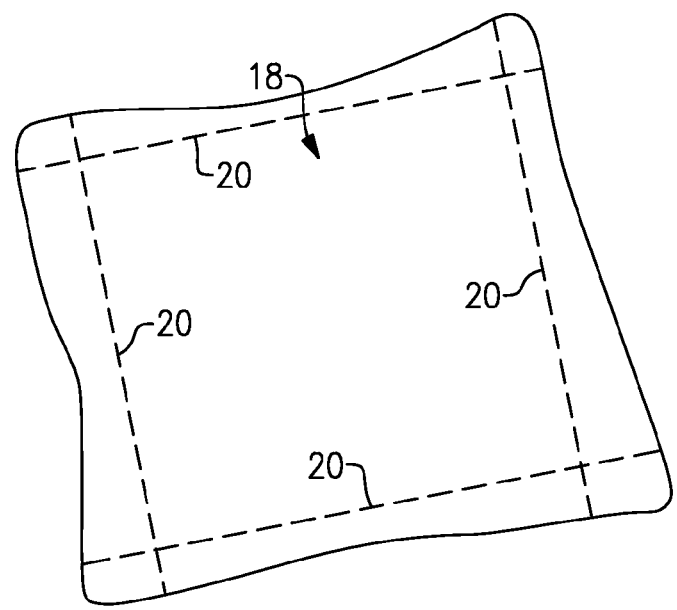
FIG. 3 schematically illustrates sizing a graft for resurfacing a bone.

FIG. 1 illustrates a joint 10 of the human musculoskeletal system. The joint 10 may be any joint found in the musculoskeletal system of the human body. In a non-limiting embodiment, the joint 10 is an ankle joint that includes a tibia 12 and a talus 14 that supports the tibia 12. Other bones may be associated with the ankle joint, including but not limited to, the calcaneus 15, the cuboid 17 and the fibula 19. The talus 14 acts as the primary load bearing surface for transferring loads from the tibia 12 through the entire foot. Because of this, over time, arthritis may develop on the talus 14, such as at an articulating surface 16 of the talus 14.

This disclosure describes resurfacing techniques for resurfacing bone, such as the talus, the patella (see FIG. 11) or any other bone, in order to reduce the pain associated with arthritis. The arthritis may be caused by repetitive trauma to the joint 10, such as may be experienced during sporting activities. Although resurfacing of the talus and patella are described throughout this disclosure as example resurfacing techniques, this disclosure is not intended to be limited to such embodiments. In other words, the various techniques and instrumentation described herein may be used to resurface any bone of any joint of the human musculoskeletal system.

FIGS. 2-10, with continued reference to FIG. 1, schematically illustrate an exemplary bone resurfacing procedure. In one non-limiting embodiment, the bone resurfacing procedure is an arthroscopic procedure. The exemplary bone resurfacing procedure is one option for treating end stage arthritis in a patient. Prior to performing the bone resurfacing procedure, appropriate radiological studies may be conducted to determine the grade of the arthritis that has developed on the bone. Excessive arthritis, such as arthritis of grades IV and higher, may require more aggressive procedures than those proposed herein.

In one non-limiting embodiment, a replicate of the bone that requires resurfacing may be created to aid in planning and executing the bone resurfacing procedure. As shown in FIG. 2, a radiographical image 21 may be obtained of the bone that is to be resurfaced, which in this example is the talus 14. The radiographical image 21 could be obtained using computed tomography (CT), magnetic resonance imaging (MRI) or any other imaging technique.

The radiographical image 21 may next be communicated for additional processing. For example, the radiographical image 21, and its underlying data, could be sent to a computer system 23 equipped with appropriate modeling software for processing the radiographical image 21. Processing may include subtracting non-critical elements and noise from the radiographical image 21, smoothing or modifying surface features, etc., to generate a 3D model 25 of the talus 14.

The 3D model 25 can be sent to a rapid prototyping system 27 to create a bone replicate 29 of the talus 14. The 3D model 25 provides the necessary numerical data for manufacturing the bone replicate 29. The rapid prototyping system 27 could be a stereolithography (SLA) system or any other rapid prototyping system. In one non-limiting embodiment, the rapid prototyping system 27 utilizes a powder resin that is selectively sintered by a laser of the rapid prototyping system 27 in a layer-by-layer fashion to generate the bone replicate 29. The bone replicate 29 can be made from a plastic material or any other suitable material.

Once created, the bone replicate 29 can be used to plan and execute the bone resurfacing technique. For example, referring now to FIGS. 1, 2 and 3, a graft 18 may be sized and shaped to generally match the articulating surface 16 of the talus 14 using the bone replicate 29. The bone replicate 29 can also be used to practice drilling and fixation methods by using trial grafts. Alternatively, in another non-limiting embodiment, a CT scan or other computerized image of the patient's joint 10 may be used to estimate the size and shape of the graft 18.

Various cutting lines 20 may be marked on the graft 18 using a marker or other writing utensil to outline the desired shape of the graft 18. The graft 18 may then be cut to the desired size and shape using any known cutting device or cutting methodology. In another non-limiting embodiment, the radiographical image 21 can be used to model and create a patient specific cutting jig/device to precisely cut the graft 18 to a desired shape to enable the surgeon to quickly create the desired shape intraoperatively. The cutting jig/device could be marked circumferentially with reference features or numbers that would correspond to the portions of the graft 18 that require stitching so that marking the graft 18 and anchoring alignment would be facilitated once inserted into the joint. Alternatively, in another non-limiting embodiment, a tissue bank could create and send the precise shaped graft 18, customized to the patient, to the surgical facility for use during surgery.

In one non-limiting embodiment, the graft 18 is an acellular dermal extracellular matrix. ArthroFlex®, sold by Arthrex, Inc., is one type of graft suitable for use in the exemplary bone resurfacing procedures of this disclosure.

Figure 4:
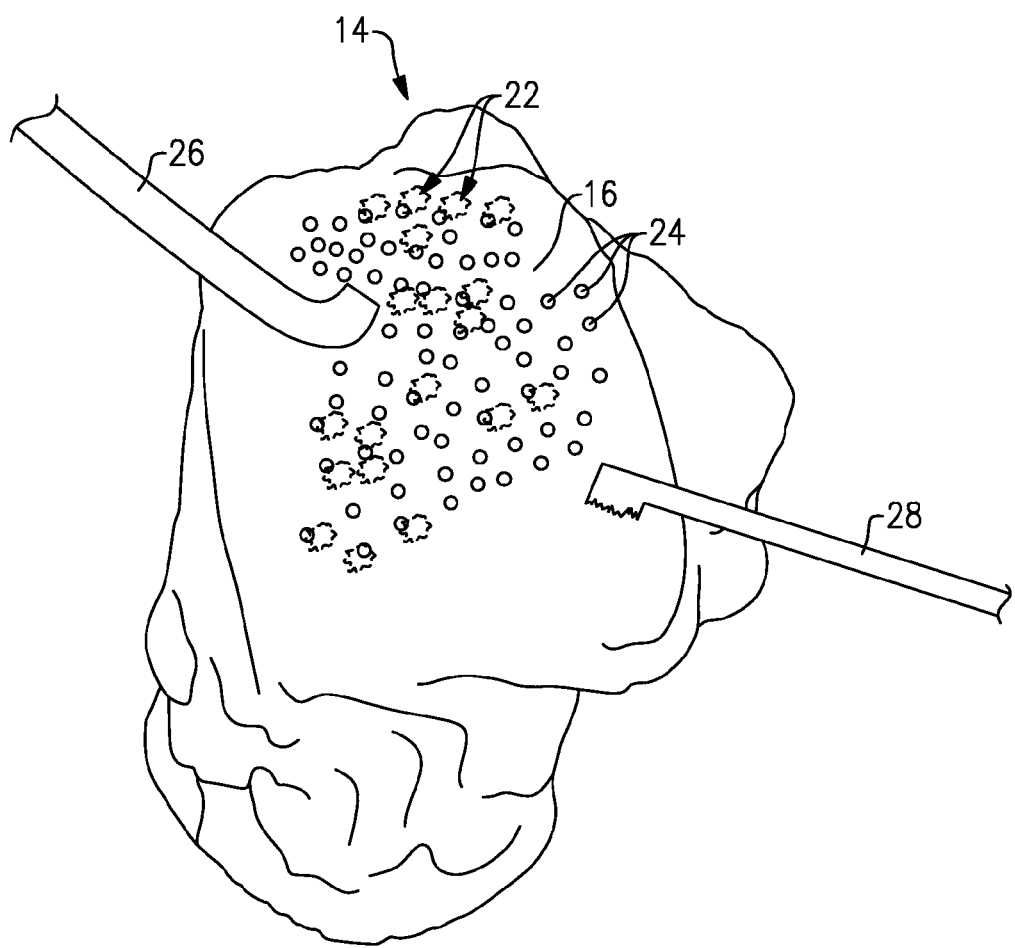
FIG. 4 schematically illustrates preparing a bone for receiving the graft of FIG. 3.

The articulating surface 16 of the talus 14 is next prepared for receiving the graft 18. As shown in FIG. 4, the talus 14 may be prepped by performing bone marrow stimulation. For example, a microfracture procedure or some other technique may be performed to obtain a bleeding bone bed 22. During the microfracture surgery, multiple perforations 24 are created on the articulating surface 16 of the talus 14. The bleeding bone bed 22 may be created using a tool 26, such as Arthrex's Powerpick™, to create the perforations 24. Formation of the perforations 24 creates the bleeding bone bed 22, which stimulates bone marrow seepage at the repair site. In another non-limiting embodiment, the bleeding bone bed 22 may be created via abrasion arthroplasty or by debriding the bone surface using a mechanized burr. Other techniques can also be used to create the bleeding bone bed 22, including but not limited to, drilling, hammering, curetting, scraping, etc.

In another non-limiting embodiment, the talus 14 may optionally be further prepared for receiving the graft 18 by debriding the articulating surface 16. The debriding procedure may be performed using another tool 28, such as Arthrex's PowerRasp™.

FIG. 5 illustrates the positioning of a drill guide 30 relative to the talus 14. The drill guide 30 may include a bracket 32, an arm 34 rotatable relative to the bracket 32 and a cannula guide 36 moveable within a slot 38 of the bracket 32. A cannula 40 may be received through the cannula guide 36 and a marking hook 42 may extend from the arm 34. In one non-limiting embodiment, the drill guide 30 is positioned relative to the talus 14 by seating a distal hook 44 of the marking hook 42 on a posterior rim 46 of the talus 14 at a location just below the articulating surface 16. The cannula 40 may be positioned at a desired location of the medial rim 48 of the talus 14 by moving the cannula guide 36 within the slot 38 of the bracket 32.

Figure 6A:
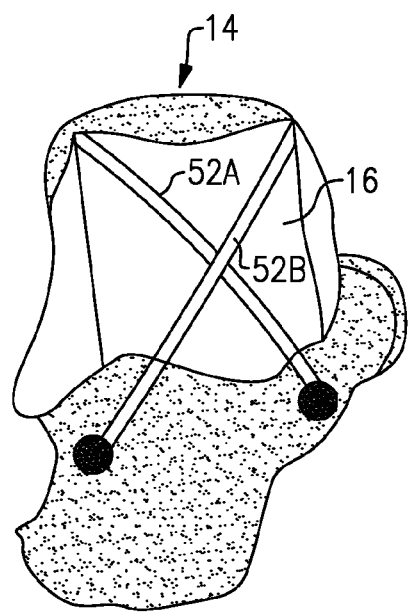
FIGS. 6A and 6B illustrate the formation of bone tunnels and the passing of sutures through a bone during a bone resurfacing procedure.

Referring now to FIGS. 5 and 6A, a drill 50 may be inserted through the cannula 40 to prepare tunnels 52A, 52B through the talus 14 beneath the articulating surface 16 (see FIG. 6A). Although not shown, a depth sleeve may be used in conjunction with the cannula 40 to control the depth of insertion of the drill 50 up to the distal hook 44 of the marking hook 42. In one non-limiting embodiment, the tunnels 52A, 52B are transosseous or crossing drill tunnels. For example, one of the tunnels 52A, 52B may exit from the posteriomedial corner of the talus 14, whereas the other of the tunnels 52A, 52B may exit from the posteriolateral corner of the talus 14.

Figure 6B:
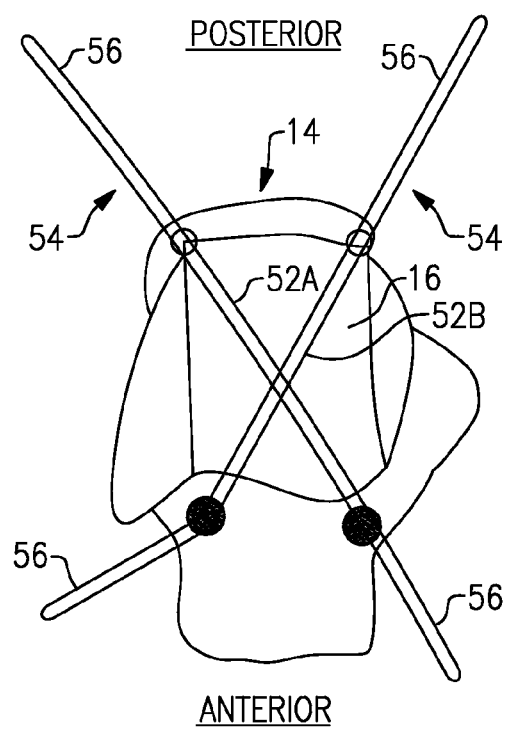

As shown in FIG. 6B, a shuttling device 54 may be passed through each of the tunnels 52A, 52B. In one non-limiting embodiment, the shuttling devices 54 are lassos made of either wire or suture. In another non-limiting embodiment, portions of the shuttling devices 54 are stiffened to simply passage of the shuttling devices 54 through the tunnels 52A, 52B. Each shuttling device 54 may include looped ends 56. The shuttling devices 54 may be advanced through a cannulation (not shown) of the drill 50 and then fed through the tunnels 52A, 52B from the anterior direction toward the posterior direction. Other insertion techniques may also be utilized. The looped ends 56 of the shuttling devices 54 that exit the tunnels 52A, 52B on the posterior side of the talus 14 may then be retrieved through an arthroscopic portal for subsequent use to position the graft 18 within the joint space.

Figure 7:
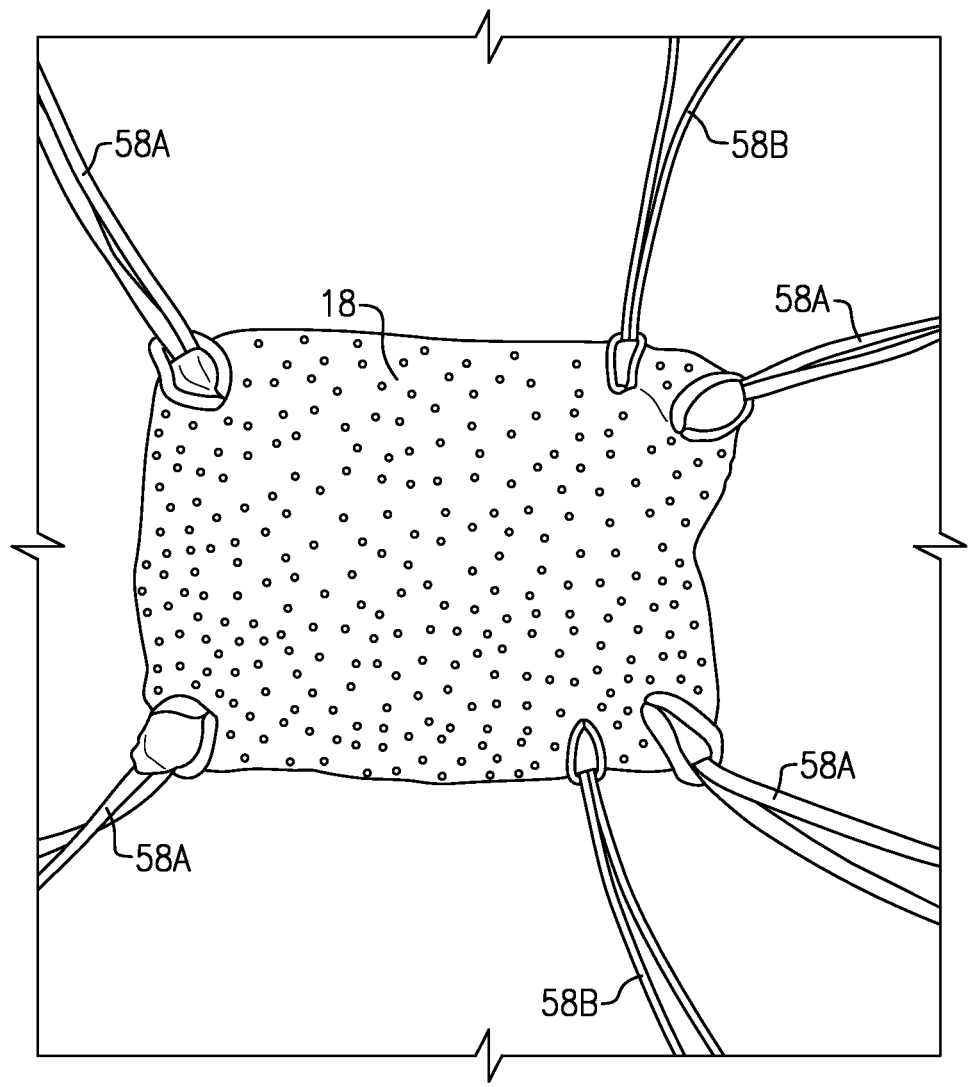
FIG. 7 illustrates preparation of a graft for positioning the graft against a surface of a bone during a bone resurfacing procedure.

FIG. 7 illustrates preparation of the graft 18 for its passing into the joint space to resurface the articulating surface 16 of the talus 14. A plurality of flexible strands 58A, 58B may be attached to the graft 18 to aid in the placement of the graft 18 over the articulating surface 16 of the talus 14. In one non-limiting embodiment, the flexible strands 58A are suture tapes and the flexible strands 58B are sutures. The flexible stands 58A may be attached to each corner of the graft 18, and one or more of the flexible strands 58B may be attached to the graft between the flexible strands 58B along a periphery of the graft 18. The flexible strands 58A aid in passing the graft 18 into the joint space, and the flexible strands 58B provide additional fixation options. Other suture configurations than shown in FIG. 7 are contemplated within the scope of this disclosure.

Figure 8:
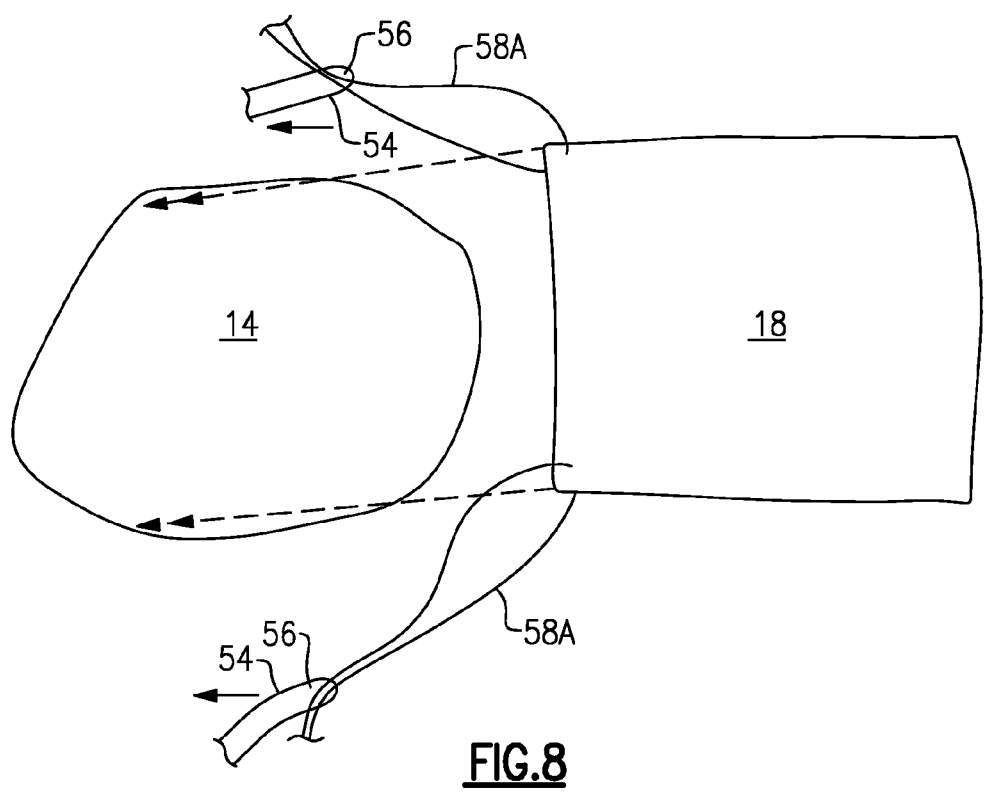
FIG. 8 schematically illustrates the positioning of a graft against an articulating surface of a bone during a bone resurfacing procedure.

Referring now to FIG. 8, the graft 18 may be pulled into place within the joint space using the shuttling devices 54 and the flexible strands 58A. In one non-limiting embodiment, ends of each flexible strand 58A are looped through one of the looped ends 56 of the shuttling devices 54. The opposite looped ends 56 from those receiving the flexible strands 58A are then pulled to shuttle the flexible strands 58A into the tunnels 52A, 52B and thereby pull the graft 18 into place over the talus 14. Prior to pulling the flexible strands 58A into the place, the graft 18 may be partially folded to ease insertion through a small incision, which may be an anterolateral or anteromedial incision. Once the graft 18 is fully seated on the talus 14, anatomic coverage of the graft 18 may be confirmed arthroscopically. In another non-limiting embodiment, intra-portal atraumatic capsular and soft tissue retraction methods and devices, such as soft cannulas, percutaneous retraction stitches, flexible cannulas, etc., are used to lift away soft tissue from the work area and create space for graft introduction and manipulation followed by bone preparation and graft anchoring.

Figure 9:
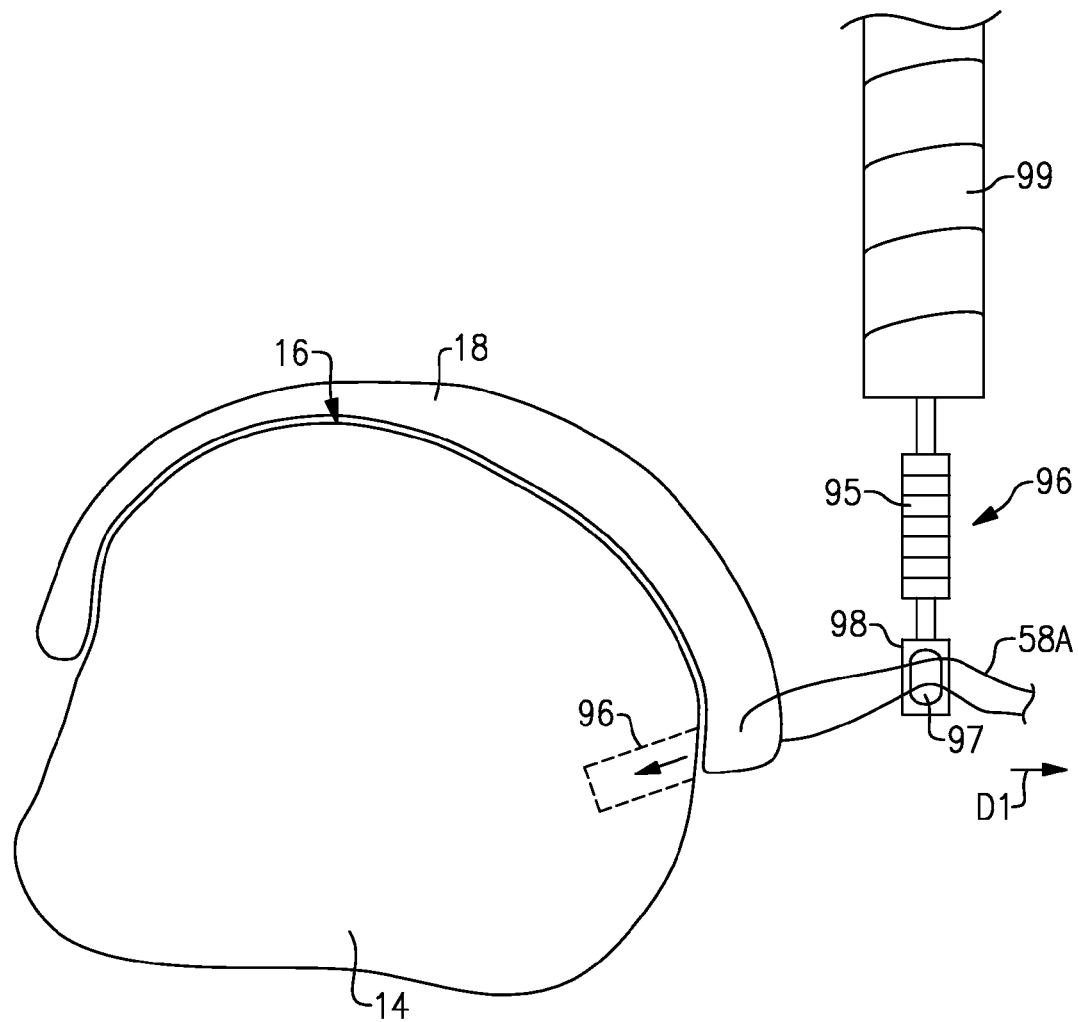
FIG. 9 schematically illustrates securing of the graft to a bone during a bone resurfacing procedure.

FIG. 9 illustrates fixation of the graft 18 to the talus 14 using one or more suture anchors 94. The graft 18 may be affixed to the articulating surface 16 of the talus 14 after confirming proper seating of the graft 18. The suture anchors 94 may be any suture anchor type or combination of suture anchors types. In one non-limiting embodiment, the suture anchors 94 are knotless suture anchors.

Holes 96 may optionally be pre-formed around a periphery of the talus 14 and below the edge of the graft 18 for receiving the suture anchors 94. Each hole 96 is configured to receive one of the suture anchors 94. A drill and other tools may be used to form the holes 96.

Next, the flexible strands 58A are loaded through a portion 98 of the suture anchor 94. The suture anchors 94 may be passed into the joint space via an arthroscopic portal 99. In one non-limiting embodiment, the portion 98 of the suture anchor 94 includes an eyelet 97. After receiving the flexible strand 58A, the eyelet 97 may be inserted into one of the holes 96. Once the eyelet 97 is positioned at least partially in the hole 96, the flexible strand 58A is tensioned in a direction D1 to approximate the graft 18 to the talus 14. Next, an anchor body 95 of the suture anchor 94 may be moved toward the eyelet 97 to trap the flexible strand 58A between the talus 14 and the anchor body 95 in order to fixate the graft 18. The procedure just described can be repeated to implant multiple suture anchors 94 to fully fixate the graft 18 to the talus 14. Although suture anchors are illustrated in this embodiment, it should be understood that fixation of the graft 18 could alternatively or additionally be achieved via the use of trans-osseous tunnels to tie suture or other filament over flush fixation devices such as buttons, staples, screws, etc. In yet another non-limiting embodiment, graft to soft tissue anastomosis could be used for fixating the graft 18 to nearby soft tissue connected to the talus 14.

Figure 10:
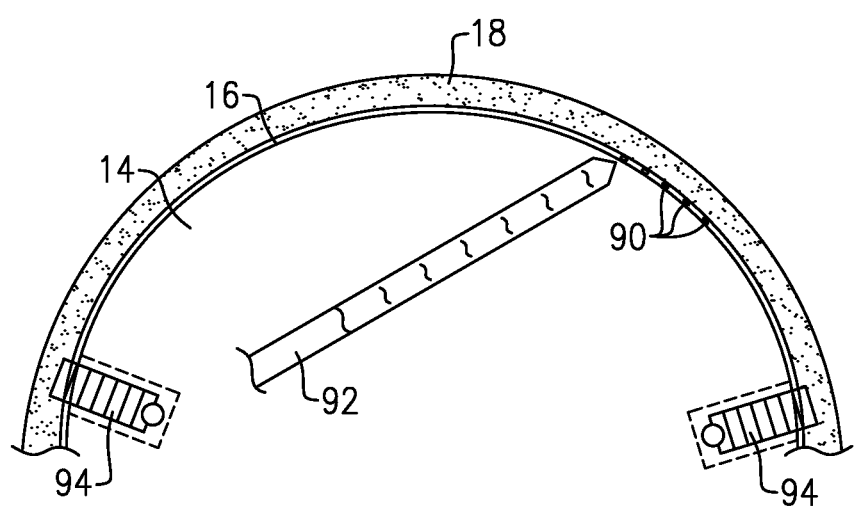
FIG. 10 illustrates application of a bone marrow concentrate to a resurfaced bone.

In another non-limiting embodiment, as shown in FIG. 10, a bone marrow concentrate 90 that has been previously harvested from the patient may be injected under the graft 18 (i.e., between the graft 18 and the articulating surface 16 of the talus 14) after the graft 18 has been properly seated. The bone marrow concentrate 90 may be applied using an applicator 92. Alternatively, the graft 18 may be soaked or impregnated with biologic blood components from the patient prior to inserting and attaching the graft 18 to the talus 14.

Figure 11:
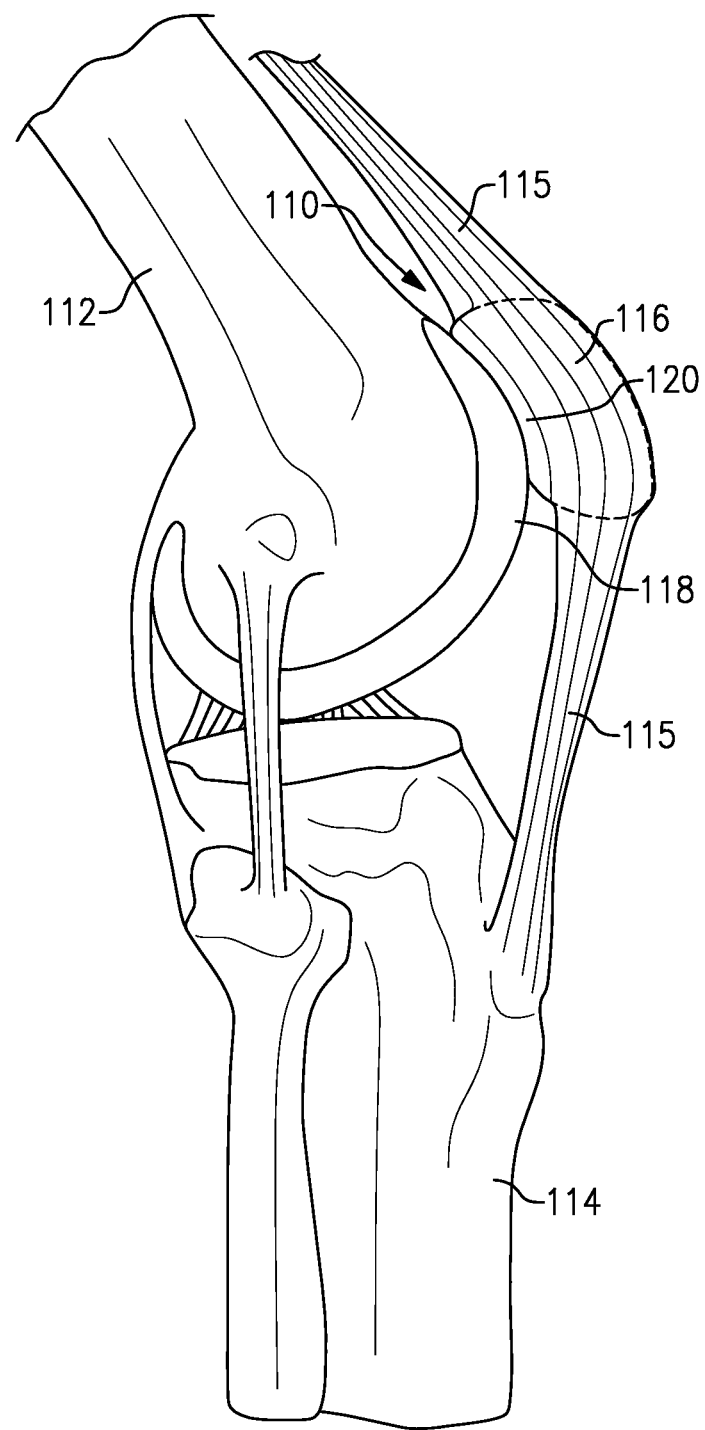
FIG. 11 illustrates another joint of a human musculoskeletal system.

FIG. 11 illustrates another joint 110 of the human musculoskeletal system. In this non-limiting embodiment, the joint 110 is a knee joint that includes a femur 112, a tibia 114 and a patella 116. Various tendons 115 (quadriceps, patellar, etc.) may extend between bones and muscles of the joint 110. The patella 116 articulates with the femur 112 and covers and protects an anterior articular surface 118 of the femur 112. Because of this, over time, arthritis and associated loss of articular cartilage may develop on the patella 116, such as at a posterior articulating surface 120 of the patella 116. This embodiment describes a resurfacing technique for resurfacing the patella 116 in order to reduce the pain associated with arthritic or diseased bone.

FIGS. 12-19, with continued reference to FIG. 11, schematically illustrate another exemplary bone resurfacing procedure. In one non-limiting embodiment, the bone resurfacing procedure is an arthroscopic procedure that may be performed through various arthroscopic portals that provide access to an internal joint space. The exemplary bone resurfacing procedure is one option for treating a patient suffering from arthritis. Prior to performing the bone resurfacing procedure, appropriate radiological studies may be conducted to determine the grade of arthritis that has developed within a patient's joint. Excessive arthritis, such as arthritis of grades IV and higher, may require more aggressive procedures than those proposed herein.

Figure 12:
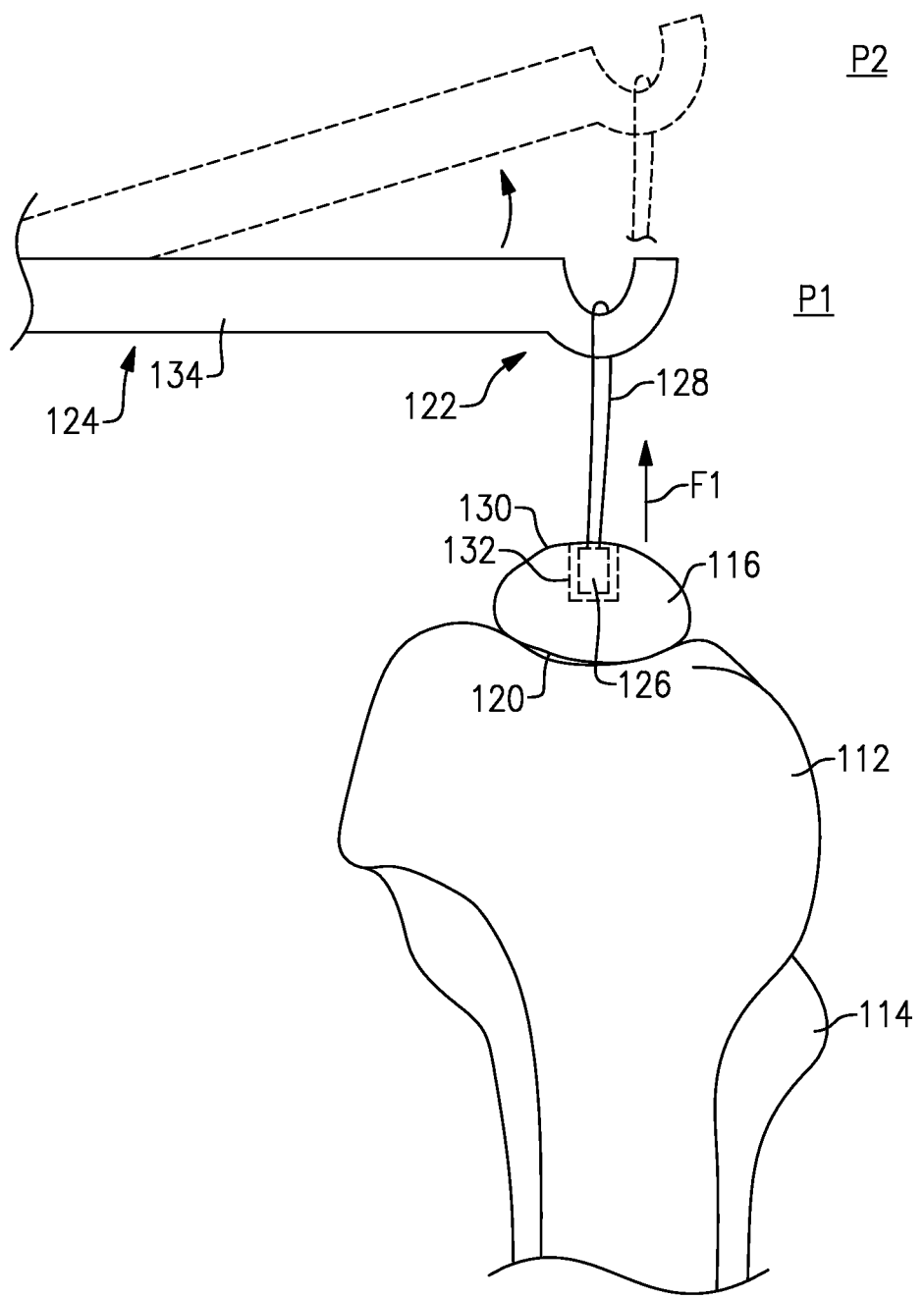
FIG. 12 schematically illustrates distraction of a bone of a joint.
Figure 13A:
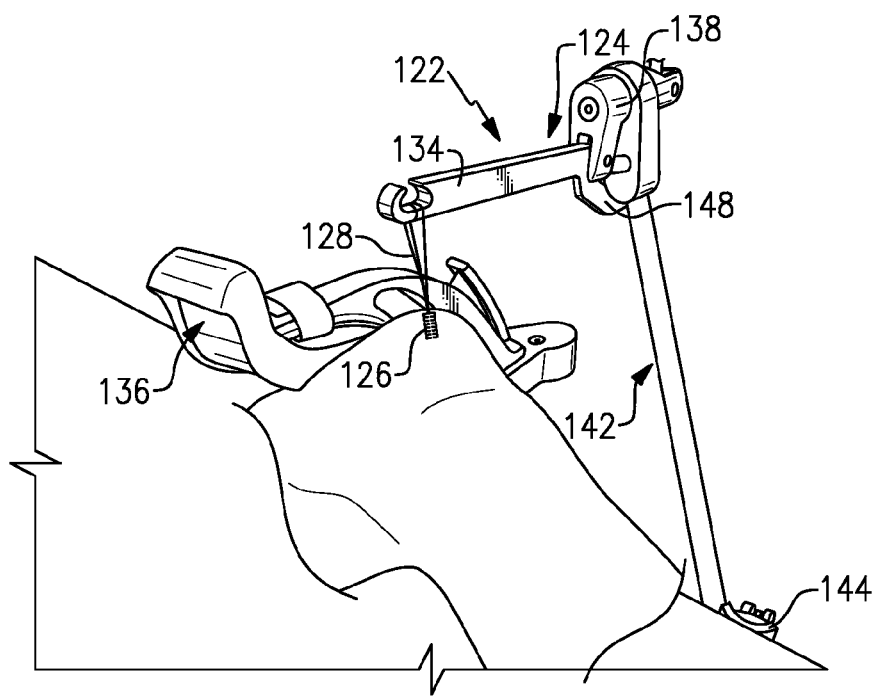
FIGS. 13A and 13B illustrate a surgical system for distracting a bone of a joint.
Figure 13B:
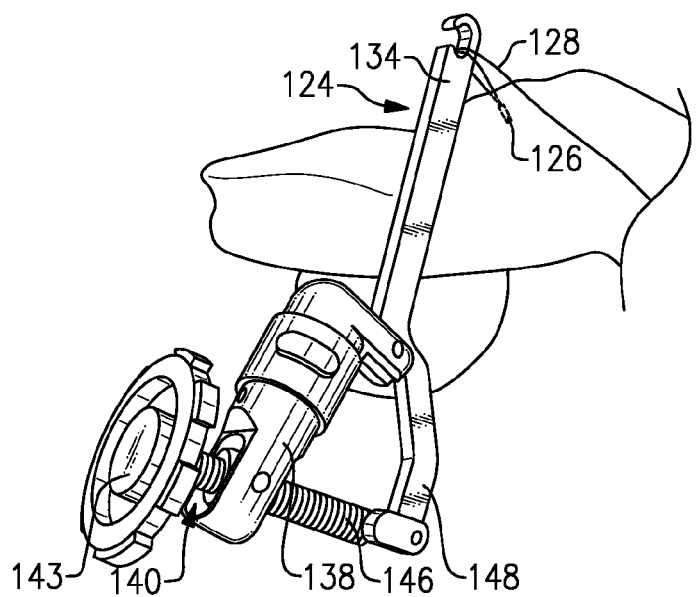

Referring first to FIGS. 12, 13A and 13B, the patella 116 may be distracted away from the femur 112 using a surgical system 122. The patella 116 is distracted away from the femur 112 to gain access to the posterior articulating surface 120. The posterior articulating surface 120 may need resurfaced because of the development of arthritis. In one non-limiting embodiment, the surgical system 122 includes a limb positioner 124, a suture anchor 126, and at least one flexible strand 128 connected between the limb positioner 124 and the suture anchor 126. The surgical system 122 is configured to apply a vertical force F1 to the patella 116 to lift it away from the femur 112.

In one non-limiting embodiment, the suture anchor 126 is inserted near a center of an anterior surface 130 of the patella 116. Any type of suture anchor may be used. In addition, although only a single suture anchor is shown in FIG. 12, a plurality of suture anchors could be utilized during the exemplary distraction procedure. A pilot hole 132 may optionally be pre-drilled into the patella 116 for inserting the suture anchor 126. Once inserted, the suture anchor 126 is fixated within the patella 116. The flexible strand 128, which may include one or more sutures, may be attached to the suture anchor 126 either before or after its insertion into the pilot hole 132.

The flexible strand 128 is next looped over an arm 134 of the limb positioner 124. The arm 134 may be moved, such as by pivoting, between a first position P1 and a second position P2 (shown in phantom in FIG. 12) to distract the patella 116 away from the femur 112. Because the suture anchor 126 is fixated inside the patella 116, movement of the arm 134 tensions the flexible strand 128 to apply the vertical force F1 to the patella 116. In another non-limiting embodiment, a holding device 136 of the surgical system 122 may optionally be employed to act as a partial counter force during the distraction procedure (see FIG. 13A). The holding device 136 may be positioned relative to either the femur 112 or the tibia 114.

Additional details of the limb positioner 124 of the surgical system 122 are shown in FIGS. 13A and 13B. The limb positioner 124 may include a body 138, the arm 134, an adjustment device 140 and a stand 142. The stand 142 includes an attachment device 144 for attaching the limb positioner 124 to a sturdy surface, such as a bed rail. The body 138 is attached to an opposite end of the stand 142 from the attachment device 144. The arm 134 may be pivotally connected to the body 138. The adjustment device 140, which includes a knob 143 and a threaded portion 146, may be used to change the positioning of the arm 134. For example, in one non-limiting embodiment, the knob 143 may be turned to advance the threaded portion 146 relative to the body 138. The threaded portion 146 is connected to an extension 148 of the arm 134, and the arm 134 is pivoted as the threaded portion 146 is advanced.

Figure 14:
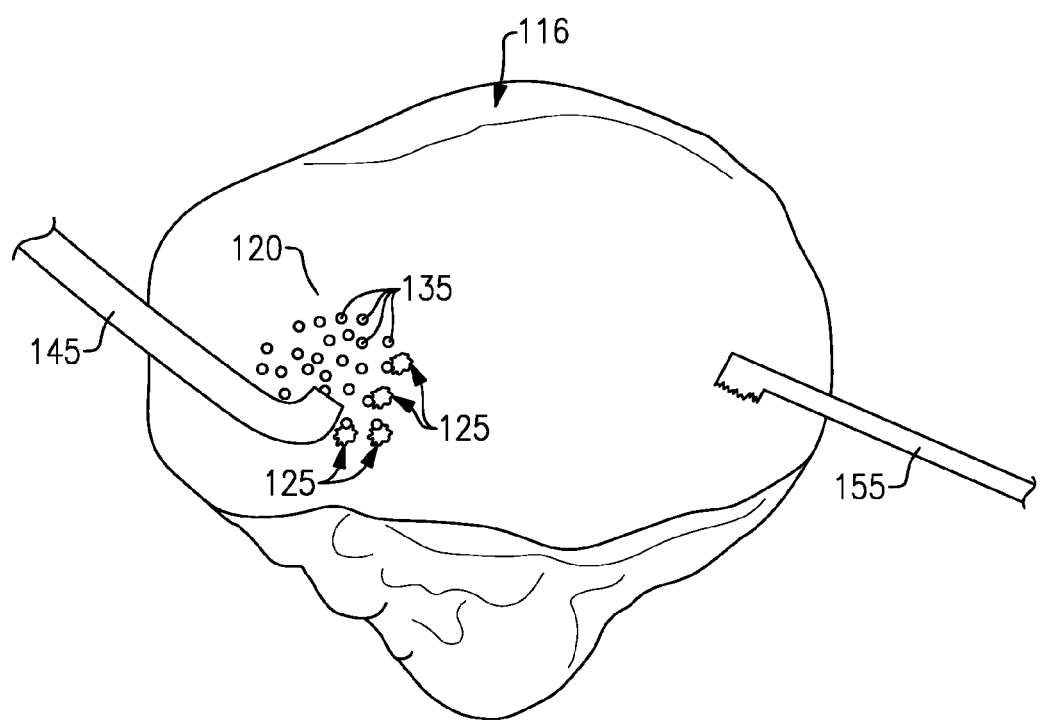
FIG. 14 schematically illustrates preparing a bone for receiving a graft during a bone resurfacing procedure.
Figure 15A:
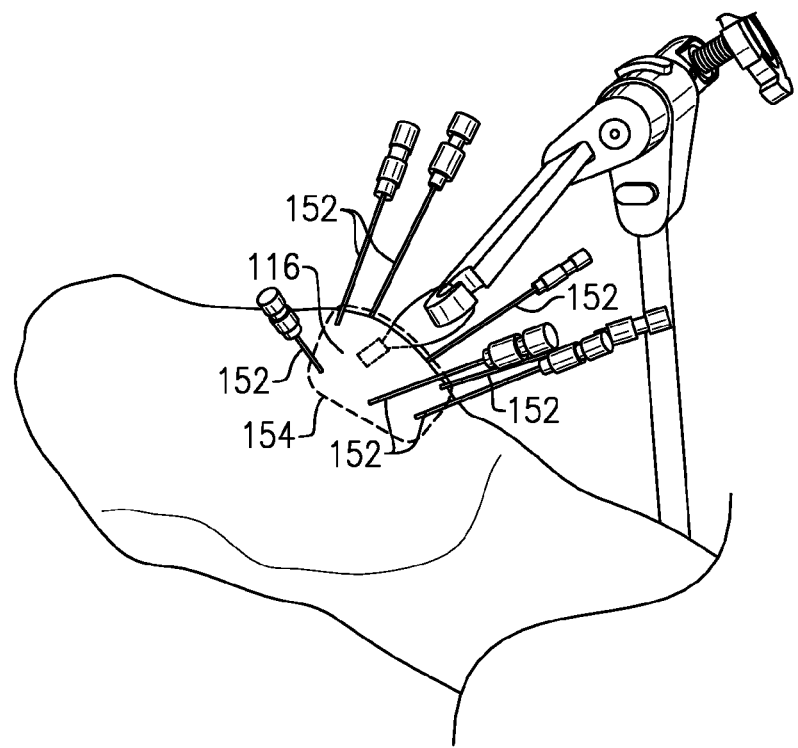
FIGS. 15A and 15B schematically illustrate preparation of a graft for positioning the graft against a surface of a bone during a bone resurfacing procedure.
Figure 15B:
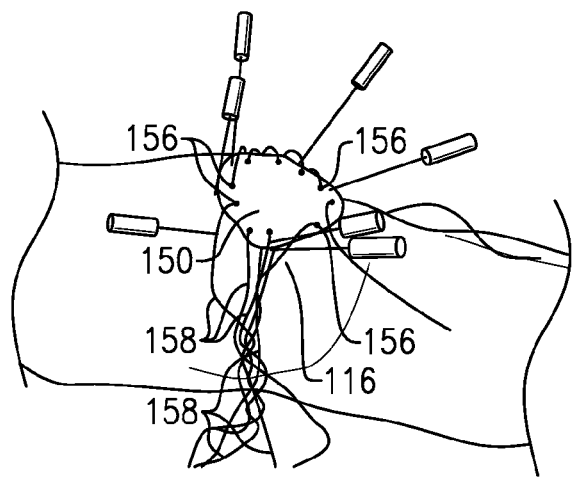

The posterior articulating surface 120 of the patella 116 may be prepared for receiving a graft 150 (see FIG. 15B). This may be done any time after distracting the patella 116 from the femur 112. As shown in FIG. 14, the patella 116 may be prepared by performing bone marrow stimulation. For example, a microfracture procedure or some other technique may be performed to obtain a bleeding bone bed 125. During the microfracture surgery, multiple perforations 135 are created on the posterior articulating surface 120 of the patella 116. The bleeding bone bed 125 may be created using a tool 145 to create the perforations 135. Formation of the perforations 135 creates the bleeding bone bed 125, which stimulates bone marrow seepage at the repair site. Other techniques can also be used to create the bleeding bone bed 125, including but not limited to, drilling, hammering, curetting, scraping, etc.

In another non-limiting embodiment, the patella 116 may be further prepared for undergoing resurfacing by debriding the posterior articulating surface 120. The debriding procedure may be performed using another tool 155.

Referring to FIGS. 15A and 15B, a graft 150 may be sized and shaped to generally match the posterior articulating surface 120 of the patella 116. In one non-limiting embodiment, the graft 150 is an acellular dermal extracellular matrix. Other graft types are also contemplated.

In one non-limiting embodiment, the graft 150 is sized and shaped using a bone replicate of the patella 116 that can be manufactured in a manner similar to that shown in FIG. 2. In another non-limiting embodiment, the size and shape of the patella 116 is visualized by outlining the patella 116 with a plurality of needles 152. The actual number of needles 152 used during this procedure could vary from patient to patient and therefore is not intended to limit this disclosure. A flexible strand 154 (shown using dashed lines in FIG. 15A) could optionally be wrapped around the outsides of the needles 152. The length of the flexible strand 154 may then be used to estimate a circumference of the patella 116. This calculated circumference can then be used to cut the graft 150 to a desired size and shape. In an alternative, non-limiting embodiment, the surface area of the patella 116 (or any other bone) could be arthroscopically visualized and measured using an articulating or extending measuring device.

As shown in FIG. 15B, the graft 150 may be placed over the patella 116 (ex-situ) between the needles 152. Markings 156 may be made around the periphery of the graft 150. The markings 156 correspond to the locations of the needles 152. The markings 156 may be made using a marker or any other writing utensil. Flexible strands 158, such as suture, suture tape, or other strands, may next be passed through the graft 150 at the location of each marking 156. Any known suture passer may be employed to pass and retrieve the flexible strands 158. The needles 152 and the flexible strands 158 may be left in place for later use to arthroscopically shuttle the graft 150 into the joint space.

Figure 16:
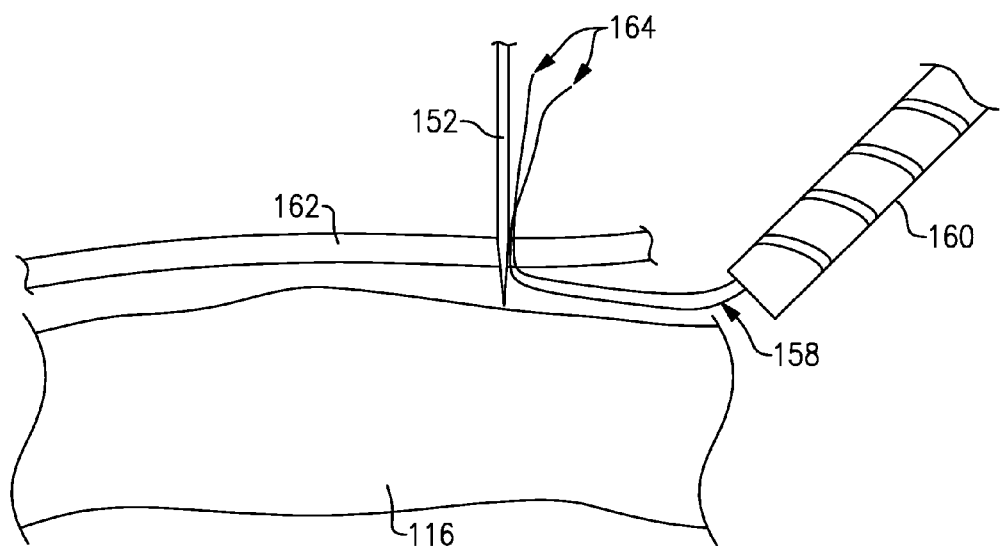
FIG. 16 schematically illustrates shuttling a flexible strand into a joint space during a bone resurfacing procedure.

FIG. 16 schematically depicts arthroscopically shuttling the flexible strands 158 into the joint space. The flexible strands 158 are shuttled into the joint space one by one and are kept separate from one another ex-situ to prevent tangling. In one non-limiting embodiment, the flexible strands 158 are individually passed through an arthroscopic portal 160 to enter the joint space. Free ends 164 of the flexible strands 158 may then be extracted through the patient's skin 162 at a location of the needle 152 that corresponds to the flexible strand 158 being passed. Various surgical instruments, including but not limited to graspers, elevators, etc., may be used to shuttle and extract the flexible strands 158 in the manner previously described. Once each flexible strand 158 has been passed, the needles 152 are removed.

Figure 17:
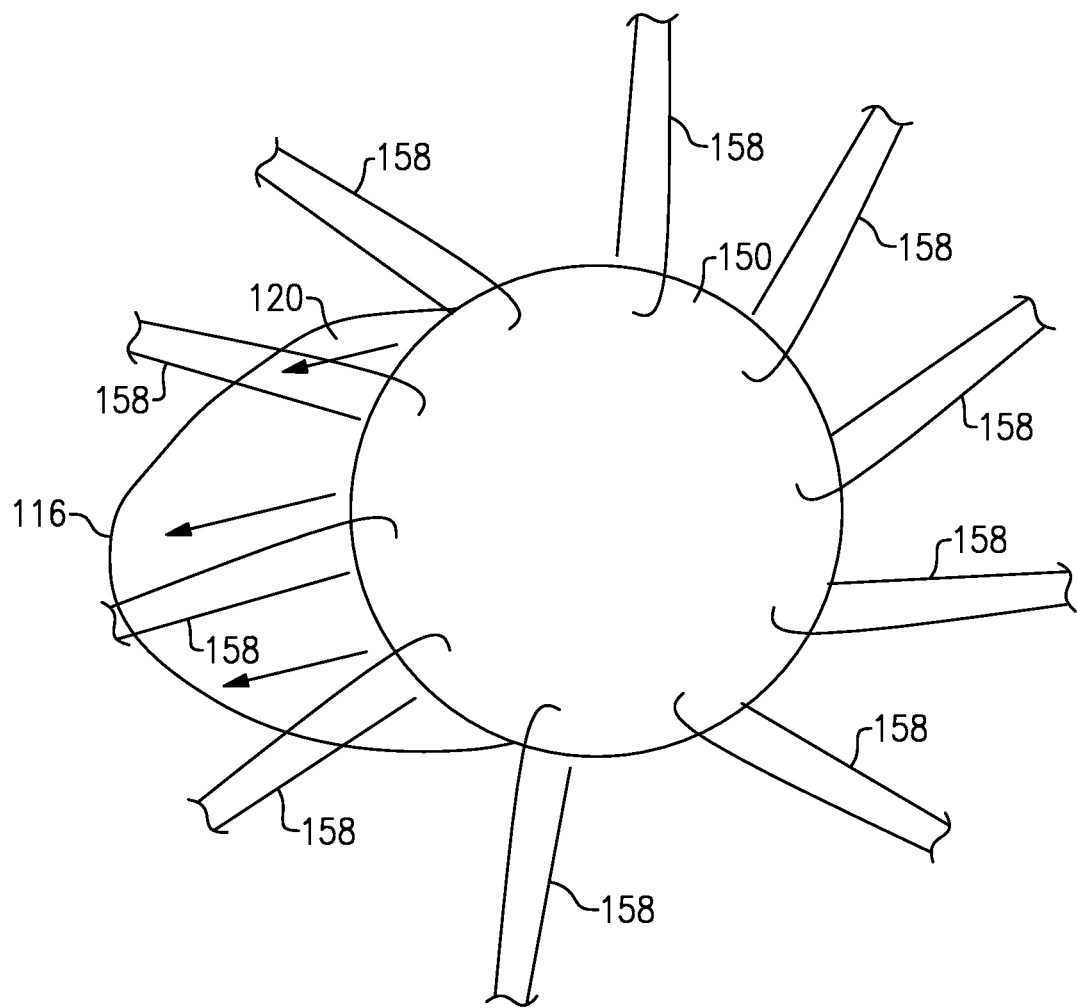
FIG. 17 schematically illustrates passing a graft into a joint space during a bone resurfacing procedure.

After each flexible strand 158 has been shuttled into the joint space, the graft 150 may be pulled into place by pulling each flexible strand 158. This step is schematically shown in FIG. 17. Prior to pulling the flexible strands 158 to position the graft 150, the graft 150 may be partially folded to ease insertion through a small incision, which may be made laterally or medially. Once the graft 150 is fully seated on the posterior articulating surface 120 of the patella 116, anatomic coverage of the graft 150 may be confirmed arthroscopically.

Figure 18:
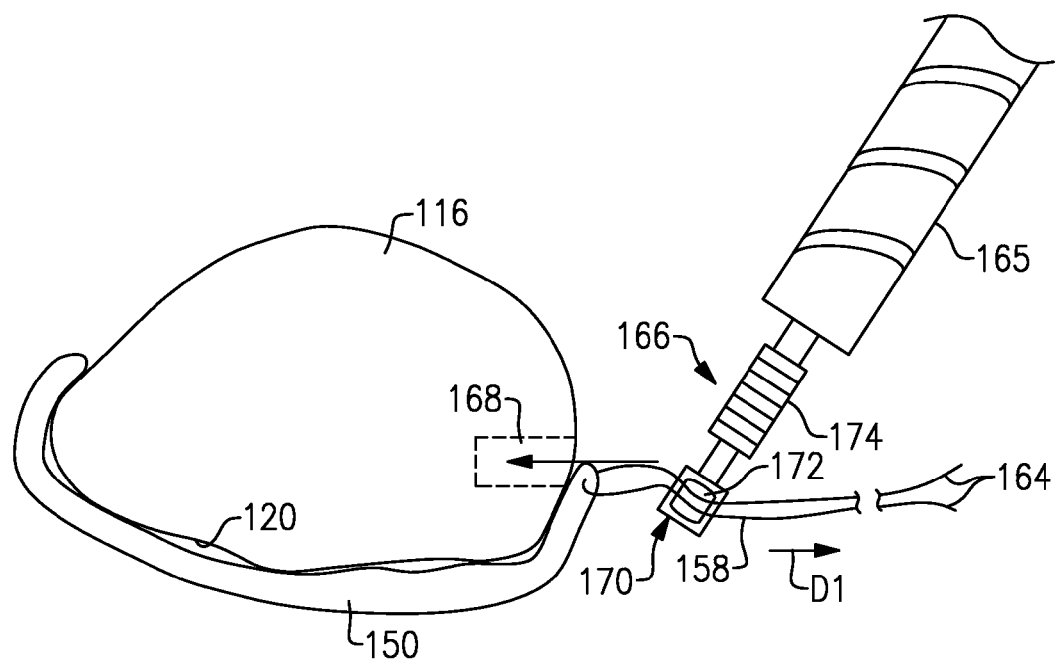
FIG. 18 illustrates securing the graft to an articulating surface of the bone during a bone resurfacing procedure.

FIG. 18 illustrates fixation of the graft 150 to the patella 116 using one or more suture anchors 166. The graft 150 may be affixed to the posterior articulating surface 120 of the patella 116 after confirming proper seating of the graft 150. The suture anchors 166 may be any suture anchor type or combination of suture anchors types. In one non-limiting embodiment, the suture anchors 166 are knotless suture anchors.

Holes 168 may optionally be pre-formed around a periphery of the patella 116 for receiving the suture anchors 166. Each hole 168 is configured to receive one of the suture anchors 166. A drill may be used to form the holes 168 in the patella 116.

Next, the free ends 164 of one of the flexible strands 158 are pulled back through the skin and are loaded through a portion 170 of the suture anchor 166. The suture anchors 166 may be passed into the joint space via an arthroscopic portal 165. In one non-limiting embodiment, the portion 170 of the suture anchor 166 includes an eyelet 172. After receiving the free ends 164 of the flexible strand 158, the eyelet 172 may be inserted into one of the holes 168. Once the eyelet 172 is positioned at least partially in the hole 168, the flexible strand 158 is tensioned in a direction D1 to approximate the graft 150 to the patella 116. Next, an anchor body 174 of the suture anchor 166 may be moved toward the eyelet 172 to trap the flexible strand 158 between the patella 116 and the anchor body 174 in order to knotlessly fixate the graft 150. The free ends 164 of the flexible strand 158 may be trimmed flush to the bone. The procedure just described can be repeated to implant multiple suture anchors 166 to fully fixate the graft 150 around the periphery of the patella 116.

Figure 19:
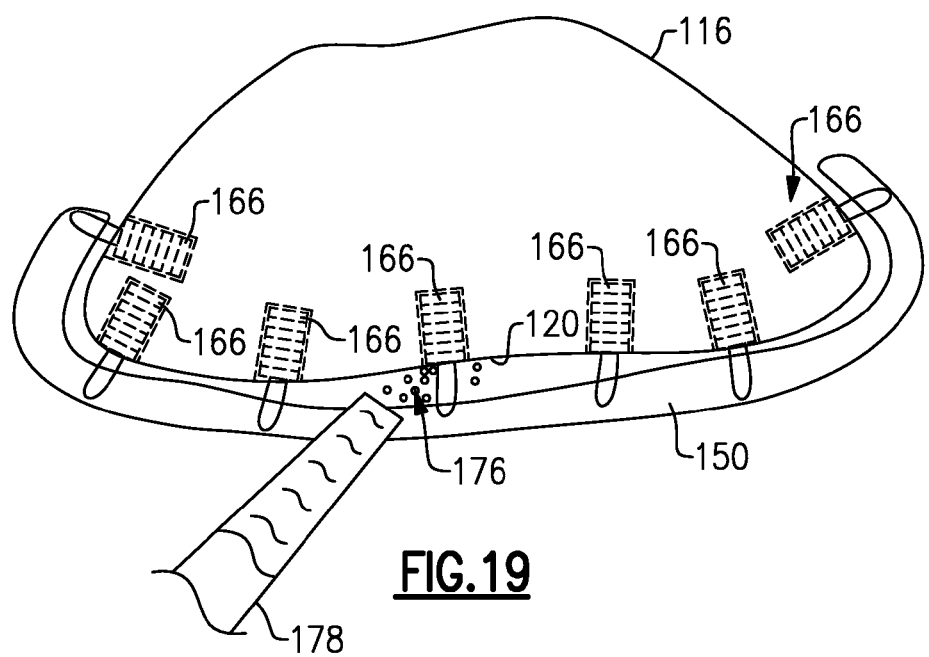
FIG. 19 illustrates application of a bone marrow concentrate to a resurfaced bone.

In another non-limiting embodiment, shown in FIG. 19, a bone marrow concentrate 176 that has been previously harvested from the patient may be injected under the graft 150 (i.e., between the graft 150 and the posterior articulating surface 120 of the patella 116) after the graft 150 has been fixated. The bone marrow concentrate 176 may be applied using an applicator 178. Alternatively, the graft 150 may be soaked or impregnated with biologic blood components from the patient prior to inserting and attaching the graft 150 to the patella 116. In yet another non-limiting embodiment, initial adhesion of the graft 150 to the patella 116 can be augmented by using a biologic glue, such as fibrin glue mixed with ACP or BMA, to accelerate adhesion and reduce the initial suture anchor loads.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method for resurfacing a bone, comprising:
   sizing a graft based on a replicate of a bone;
   arthroscopically positioning the graft against an articulating surface of the bone; and
   securing the graft to the bone using at least one suture anchor;
   wherein the bone is a patella bone and the method includes:
   passing a plurality of flexible strands through the graft;
   shuttling the plurality of flexible strands one by one into a joint space surrounding the patella bone;

extracting free ends of each of the plurality of flexible strands through skin;

pulling the graft into place against the articulating surface using the plurality of flexible strands; and anchoring the graft to the patella bone using the at least one suture anchor.

2. The method as recited in claim 1, wherein the replicate of the bone is a rapidly prototyped model of the bone.

3. The method as recited in claim 1, comprising:
obtaining a radiographical image of the bone;
communicating the radiographical image to a computer system to generate a 3D model of the bone; and
communicating the 3D model to a rapid prototyping system to create the replicate of the bone.

4. The method as recited in claim 1, comprising practicing a surgical procedure on the replicate of the bone prior to performing the steps of arthroscopically positioning the graft and securing the graft to the bone.

5. The method as recited in claim 1, wherein the graft is an acellular dermal extracellular matrix.

6. The method as recited in claim 1, wherein the at least one suture anchor is a knotless suture anchor.

7. The method as recited in claim 1, wherein sizing the graft includes cutting the graft into a desired size and shape.

8. The method as recited in claim 1, comprising debriding the articulating surface prior to the step of arthroscopically positioning the graft.

9. The method as recited in claim 1, comprising preparing drill tunnels in the bone prior to the step of arthroscopically positioning the graft.

10. The method as recited in claim 1, comprising folding the graft prior to the step of arthroscopically positioning the graft.

11. A method for resurfacing a bone, comprising:
sizing a graft based on a replicate of a bone;
arthroscopically positioning the graft against an articulating surface of the bone;
creating a bleeding bone bed on the articulating surface prior to the step of arthroscopically positioning the graft; and
securing the graft to the bone using at least one suture anchor.

12. The method as recited in claim 11, wherein the step of arthroscopically positioning the graft includes:
attaching a plurality of flexible strands to the graft; and
passing the graft into a joint space surrounding the bone using the plurality of flexible strands.

13. The method as recited in claim 12, wherein the step of passing the graft into the joint space includes shuttling the plurality of flexible strands through tunnels formed in the bone using a shuttling device.

14. The method as recited in claim 11, wherein using the at least one suture anchor includes:
passing a flexible strand through the graft;
loading the flexible strand through a first portion of the at least one suture anchor;
inserting the first portion of the at least one suture anchor into a hole formed in the bone;
tensioning the flexible strand; and
inserting a second portion of the at least one suture anchor into the hole to trap the flexible strand between the bone and the second portion.

15. A method for resurfacing a bone, comprising:
sizing a graft based on a replicate of a bone;
arthroscopically positioning the graft against an articulating surface of the bone;
securing the graft to the bone using at least one suture anchor; and
applying a bone marrow concentrate between the graft and the articulating surface after the step of securing the graft to the bone.

16. A method for resurfacing a bone, comprising:
sizing a graft based on a replicate of a bone;
arthroscopically positioning the graft against an articulating surface of the bone; and
securing the graft to the bone using at least one suture anchor;
wherein the bone is a talus bone and the method includes:
preparing crossing tunnels through the talus bone;
passing sutures through the crossing tunnels;
pulling the graft into place against the articulating surface of the talus bone using the sutures; and
anchoring the graft to the talus bone using the at least one suture anchor.

* * * * *